United States Patent [19]

Mueller et al.

[11] 4,423,099

[45] Dec. 27, 1983

[54] MEMBRANE MODIFIED HYDROGELS

[75] Inventors: Karl F. Mueller, New York; Sonia J. Heiber, Bedford Hills, both of N.Y.

[73] Assignee: Ciba-Geigy Corporation, Ardsley, N.Y.

[21] Appl. No.: 172,908

[22] Filed: Jul. 28, 1980

[51] Int. Cl.³ .................................................. B32B 11/20
[52] U.S. Cl. ...................................... 428/35; 424/19; 424/DIG. 7; 428/36; 428/306.6; 428/310.5; 428/320.2; 428/321.5; 428/322.7; 428/212; 428/218; 428/402; 428/409; 428/398; 428/407; 525/903; 525/905
[58] Field of Search ............... 525/905, 903; 428/305, 428/35, 36, 398, 402, 407, 306, 212, 218, 409, 306.6, 310.5, 321.5, 322.7, 320.2; 424/19, DIG. 7; 427/301

[56] References Cited

U.S. PATENT DOCUMENTS

| | | | |
|---|---|---|---|
| 3,578,545 | 5/1971 | Carson et al. | 428/260 |
| 3,764,363 | 10/1973 | Grandi et al. | 428/305 |
| 3,885,078 | 5/1975 | Wichterlo | 428/420 |
| 3,940,469 | 2/1975 | Steigelmann et al. | 428/398 |
| 3,954,666 | 5/1976 | Marquisee et al. | 428/402 |
| 3,970,718 | 7/1976 | Takahashi et al. | 525/903 |
| 3,994,439 | 11/1976 | Van Breen et al. | 239/54 |
| 4,051,159 | 9/1977 | Tsoucalas et al. | 239/54 |
| 4,154,818 | 5/1979 | Kanada et al. | 424/19 |
| 4,164,560 | 8/1979 | Falkman | 424/19 |
| 4,181,694 | 1/1980 | Hashino et al. | 428/398 |
| 4,204,018 | 5/1980 | Bernstein et al. | 428/240 |
| 4,224,427 | 9/1980 | Mueller | 526/93 |
| 4,226,848 | 10/1980 | Nagai et al. | 424/19 |
| 4,245,420 | 1/1981 | Carr et al. | 428/310.5 |
| 4,265,959 | 5/1981 | Sano et al. | 428/305 |
| 4,269,713 | 5/1981 | Yamoshita et al. | 428/398 |
| 4,274,965 | 6/1981 | Carden, Jr. et al. | 428/398 |
| 4,302,553 | 11/1981 | Frisch et al. | 525/903 |

OTHER PUBLICATIONS

G. C. Berry et al., Modification of Polyurethanes by Interpenetrating Polymer Network Formation with Hydrogels, ACS Preprint, Organic Coatings and Plastics Chem., vol. 38 (1978).
D. Klempner, Interpenetrating Polymer Networks, Angew. Chem. Int. Ed. Engl. vol. 17, pp. 97–106 (1978).
G. Akovali et al., Gradient Polymers by Diffusion Polymerization, Journal of Applied Polymer Science, vol. 20, pp. 2419–2427 (1976).
C. F. Jasso et al., Stress-Strain Behavior of PMMA/-CIEA Gradient Polymers, Multiphase Polymers, pp. 443–453 (1979).

*Primary Examiner*—Ellis P. Robinson
*Attorney, Agent, or Firm*—Michael W. Glynn

[57] ABSTRACT

Non-uniform water-insoluble interpenetrating polymer blend compositions comprising a first permeable water swellable polymer substrate interpenetrated in a gradient substantially normal to the substrate surface by a second less permeable condensation polymer to form a diffusion rate controlling membrane therein. Such compositions are useful as polymers with reduced permeabilities for water and organic solvents and therefore for the controlled delivery of active ingredients such as fragrances and bio-affecting agents into air or aqueous environments, or in membrane separation processes.

20 Claims, 2 Drawing Figures

Fig. 1. Cumulative release curve for Tripelennamine-HCl from IPN modified beads of Ex. 14, Ex. 15 Ex. 16 and unmodified control monolith Fig. 1. Cumulative release curve for Tripelennamine-HCl from IPN modified beads of Ex. 14, Ex. 15, Ex. 16 and unmodified control monolith Fig. 2. Release rate of Tripelennamine-HCL vs time, of IPN modified beads of Ex. 14, Ex. 15, Ex. 16 and unmodified control monolith

MEMBRANE MODIFIED HYDROGELS

BACKGROUND OF THE INVENTION

The instant invention relates to a novel class of modified permeable water swellable polymers. Water swellable polymers belong to a genus of materials known as hydrogels.

Hydrogels have been described since 1965, e.g. U.S. Pat. No. 2,976,576, and subsequently a large number of patents have been issued describing the synthesis and use of hydrogels based primarily on 2-hydroxyethyl methacrylate and, to a lesser extent, on N-vinylpyrrolidone. Typically, these hydrogels are crosslinked, water-swellable polymers made by copolymerization of 2-hydroxyethyl methacrylate. They are used as polymeric, inert carriers for active substances, which are slowly and controllably released from these carriers; such active substances may be drugs as in U.S. Pat. Nos. 3,577,826; 3,577,512; 3,551,556; 3,520,949; 3,576,760; 3,641,237, and 3,660,563; 4,177,056; 4,192,827; agricultural chemicals, as in U.S. Pat. No. 3,576,260 or fragrances, as in U.S. Pat. Nos. 3,400,890; 3,567,118; and 3,697,643.

Their uses as body implants and bandages have also been described in U.S. Pat. Nos. 3,577,516; 3,695,921; 3,512,183; and 3,674,901. The widely used soft contact lens consists of this material, as in U.S. Pat. Nos. 3,488,111; 3,660,545; and 3,629,504.

In the pharmaceutical field the main interest lies in the slow and controllable release of drugs from such hydrogels. Drug-containing hydrogel preparations have been described as being in the form of bandages; subcutaneous implants, buccal devices, intrauterine devices, and eye inserts. They are made by complicated fabrication procedures which usually involves casting the monomer solution into a suitable mold and polymerizing in the presence of a free readical generating initiator.

The use of drug loaded hydrogel granules as an oral dose form has also been suggested in Australian 16202/67 and U.S. Pat. No. 4,177,056. It is indeed one of the most useful applications of this concept in medicine since it allows the delivery into the bloodstream of an orally taken drug to spread out over several hours in a reproducible manner. This eliminates wasteful and potentially dangerous peak drug concentrations in the blood, while prolonging the time during which preferred and effective drug levels in the blood are maintained.

Whenever active ingredients are released from a monolithic hydrogel matrix by diffusion in an aqueous medium, their release tends to follow first order kinetics, that is the release rate is ordinarily proportional to the drug concentration inside the gel; it is fastest at the very beginning and gradually slows down toward the end. While such a mechanism prolongs the release of an active ingredient and spreads it out long enough to make it useful for instance for orally taken drugs whose metabolic half-life in the body is in the order of several hours, it is not useful for delivering an active substance at a more constant rate, as is necessary for drugs whose metabolic half-life is short.

In such a case, the hydrogel, serving as the reservoir of the drug, has been covered by a membrane of lesser permeability, this membrane being laminated or coated on the surface of the hydrogel. Diffusion through this membrane is the release rate determining step, and the release rate itself is less influenced by the changing drug concentration in the hydrogel. Thus, the release rate follows a mechanism close to zero-order.

While such modified hydrogels containing a coated or laminated rate controlling membrane are useful, such membranes may peel off and delaminate under conditions of swelling and deswelling or simply burst due to osmotic pressure exerted by the dissolving active ingredient. For instance, plasma polymerization or plasma induced polymerization which can be used to deposit thin membranes on polymeric substrates characteristically results in brittle coatings which tend to peel off and suffer from poor adhesion, especially under conditions of volume expansion and contraction, as occurs during the swelling and drying operations.

DETAILED DISCLOSURE

It has now been unexpectedly discovered that hydrogels can be modified by incorporating an interpenetrating membrane therein which is less permeable than the hydrogel and which can effectively resist the stress of swelling and drying. The membrane is formed by a condensation polymer which is interwoven with the substrate hydrogel network.

Where the hydrogel is in the form of a bead, the interwoven condensation polymer network forming the active ingredient rate controlling membrane characteristically exists in form of a compositional gradient going from high concentration on or near the surface to zero inside the bead, such that the membrane compositional gradient is substantially normal to the hydrogel substrate surface.

This is most easily accomplished by imbibing the hydrogel with a reactant, followed by immersion of the hydrogel containing said reactant in a medium containing a coreactant under conditions which allow diffusion of the coreactant into the reactant imbibed hydrogel, and promote simultaneously the reaction of the coreactant to form the condensation polymer. Synthesized under such conditions, the condensation polymer is interwoven with the hydrogel substrate, thereby forming a membrane in form of an interpenetrating polymer network (IPN). The concentration of the interwoven condensation polymer and the steepness of its compositional gradient are dependent on the speed and extent of diffusion and on the rate of reaction; when diffusion is much faster than reaction then the IPN will extend deep into the polymer, while when the reaction is fast compared to diffusion, the IPN will be concentrated in a more or less narrow volume near the surface.

Where the hydrogel surface is not treated between the imbibing step and the immersion step, the hydrogel exhibits a gradient going from high concentration of the condensation polymer on the surface to a low concentration and finally zero concentration proceeding to the interior of the hydrogel. If the reactant imbibed hydrogel surface is washed with an inert solvent or diluent for the reactant so as to remove a portion of the reactant from the surface of the hydrogel prior to the immersion step, then the gradient can be modified such that there is a low concentration of condensation polymer on the surface, increasing to a maximum concentration of interwoven condensation polymer, then decreasing to zero as one proceeds further towards the interior of the hydrogel bead. As the artisan can appreciate, in either case, the gradient is substantially normal to the hydrogel substrate surface.

Where the hydrogel is in the form of a sheet or a bag, one may form the membrane by treating one surface by the reactant imbibing procedure, optionally followed by the washing process, and then treating the same surface by immersion of the hydrogel containing the reactant imbibed therein into the coreactant medium. Again the interwoven membrane is present as a gradient normal to the surface of the sheet or bag. The hydrogel imbibed with the first reactant does not have to contain this reactant uniformly distributed, but it is enough to imbibe only the surface region. If the reactant is a solid imbibed from a volatile solvent it will remain in the surface without further equilibrating after a quick drying step to remove the solvent.

Alternatively, the opposite sides of the hydrogel sheet or bag may be treated with reactant and coreactant respectively. Thus, for example, the interior of a hydrogel bag may be filled with a liquid medium containing reactant, and the bag placed in a medium containing the co-reactant. As the reactant and co-reactant diffuse from opposite sides of the bag, the condensation polymer is formed as an interwoven network at an interface inside the polymer substrate. The bag is then removed from the respective media and washed to obtain a hydrogel bag containing a less permeable membrane parallel to the respective surfaces of the bag in a gradient which is low or zero at the surfaces, going to a high concentration in the interior, and is again normal to the bag surfaces. Like sheets and bags, tubes and hollow fibers are equally well suited to be modified by GIPN's according to this invention. The active ingredients may be placed therein and the ends closed; sheets may be used to close off an active ingredient containing reservoir.

Although in most cases both interwoven polymers are crosslinked it is possible that either one or both components of the IPN are linear, non-crosslinked polymers. In a case where the substrate polymer is linear, it can be dissolved, in a suitable selective solvent leaving behind the diffusion-polycondensate as a separate, unsupported membrane of unique structure.

Alternatively, any linear and soluble diffusion polycondensate can be extracted from a non-soluble polymer matrix.

The process is properly called a diffusion polycondensation and the product is a gradient interpenetrating polymer network (referred to hereinafter as GIPN).

As illustrated above, the unique characteristics of the membrane modified polymer structure are obtained by the simultaneous occurrence of diffusion and reaction to form the condensation copolymer within the hydrogel polymer matrix, which serves as an expanded interface.

In order to promote the initial diffusion of the reactant into the hydrogel, the hydrogel matrix is advantageously swollen either prior to, or, contemporaneously with, the imbibing of the hydrogel with said reactant. In some instances the reactant itself is a swelling agent for the hydrogel. Otherwise, it is advantageous to swell the hydrogel matrix with an inert solvent thereby facilitating the diffusion of the reactant into the matrix. If an inert solvent is also used with the co-reactant the resulting solvent/coreactant solution aids the diffusion of the coreactant and facilitates control of the membrane forming reaction.

Synthesizing the GIPN in presence of a solvent has the unexpected advantage that the membrane is even better able to contract and expand without cracking, having been formed with the hydrogel in the expanded state.

Similarly unexpected was that although the swelling rate is reduced, the final degree of swelling (DS) in water or a protic solvent, such as ethanol, of the instant novel GIPN membrane modified hydrogels is almost as great as for the unmodified hydrogel. Moreover, the instant membrane modified hydrogels can be loaded with active ingredients to virtually the same level as unmodified hydrogels. This is extremely important, since it allowed the synthesis of the modified hydrogels to be followed by a washing operation to remove possible toxic or otherwise unwanted side products or unreacted materials, a procedure which could not be carried out effectively if the active ingredient had to be incorporated before the membrane is made.

In this respect, the present invention is a significant step forward over conventional known encapsulation processes, such as coacervation and interfacial polymerization, where the active ingredient is present during membrane synthesis.

Most important, it has been found that the instant novel hydrogel GIPN membrane layer containing beads, and the like, release an active ingredient over a much longer prolonged period of time with a substantial amount of the release occurring at an almost constant rate.

Although the release of an active agent from the hydrogel GIPN according to the instant invention follows close to zero-order kinetics, the exact mechanism is complex and little understood in detail.

For example, a bead loaded with a soluble drug and immersed in water will swell and therefore change its volume and surface area. At the same time the drug will dissolve and diffuse to the outside while the osmotic pressure gradient will pull more water or gastric fluid inside. After a certain time, when equilibrium swelling has been established, the net flow of water across the interface will be close to zero, although with continuing decline of drug concentration inside the bead of equilibrium water content itself can be expected to change. It is the simultaneous occurrence of these diffusion processes which leads to the observed unique drug release pattern.

Also, important is the fact that GIPN modified hydrogel surfaces are considerably hardened and strengthened.

The hydrogels useful in carryingg out the process of this invention are generally all water swellable, but water insoluble polymers. Such polymers are for instance synthesized by freeradical copolymerization of a water soluble vinyl monomer with a difunctional crosslinking agent; crosslinked poly-2-hydroxyethyl methacrylate and poly-vinylpyrrolidone are two of the most widely known and used hydrogels, but other water soluble monomers can also be used in the preparation of hydrogels as well as a large variety of comonomers and of crosslinking agents. Espcecially useful are hydrogels prepared by copolymerization with macromeric crosslinking agents, as described in U.S. Pat. No. 4,192,827. Other useful hydrogel compositions are described in U.S. Pat. Nos. 3,220,960; 3,520,949; and 3,503,942.

Water soluble vinyl monomers useful for the preparation of hydrogels include, but not exclusively, the hydroxyalkyl esters and amides of acrylic and methacrylic acid, such as 2-hydroxyethyl acrylate or methacrylate, 2- and 3-hydroxypropyl acrylate and methacrylate; 2,3-dihydroxypropyl methacrylate; compounds of structure $$H_2C=\underset{R}{C}-COO(CH_2CH_2O)_nR',$$

where R and R' are hydrogen, methyl or ethyl and n is an integer from 2–50. Hydroxyalkyl mono esters and diesters of maleic or fumaric acid, and their ethoxylated derivatives, like di-2-hydroxyethylmaleate and fumarate; and 2- and 3-hydroxypropylbutyl fumarate are similarly useful, as are hydroxy alkyl vinyl ethers, such as 2-hydroxyethyl vinyl ether and 4-hydroxybutyl vinyl ether. Other useful monomers are N-vinyl pyrrolidone and N-vinyl pyrrolidine, 4- and 2-vinyl-pyridine; N,N-dialkylamino alkyl esters and amides of acrylic and methacrylic acid, like N,N-dimethylamino ethyl methacrylate and methacrylamide; N,N-dimethylaminoethyl vinyl ether, N-methylol acrylamide, acrylic acid, methacrylic acid, sodiumstyrene and sodium vinyl sulfonate, acrylamide and methacrylamide.

These monomers can be used alone and in combination with each other, and may be copolymerized with suitable hydrophobic vinyl monomers, like styrene, acrylates and methacrylates, vinyl esters and vinyl ethers; maleates, fumarates and vinyl ethers require the presence of comonomers for polymerization to proceed. Also useful is poly-vinyl alcohol in crosslinked or linear state as well as vinyl alcohol copolymers with ethylene, acrylates, vinylesters, and vinylpyrrolidone copolymers with vinylesters.

The crosslinking agent employed in making the hydrogel may be a di- or poly-functional vinyl compound of 200–10000 molecular weight and be present in the polymerizing mixture in amounts ranging from 0.1% (for low MW crosslinkers) to 60% (for high MW crosslinkers).

Other useful hydrogel materials are polyethylene oxide containing polycondensates, such as polyurethanes from diisocyanates and polyethylene oxide diols of 300–10000 MW; polyesters from diacids, diacid chlorides or anyhdrides and polyethylene oxide diols of 300–10000 MW; unsaturated polyesters devised from maleic- or fumaric acid and polyethylene oxide diols and copolymerized with styrene or acrylic monomers to a crosslinked polymer; epoxy polymers derived from diepoxides and the 3-amino-propyl ethers of polyethylene oxide diols; polyamides from diacids, diacid chlorides and anhydrides and 3-aminopropyl ethers of polyethylene oxide diols of 300–10000 MW. By those knowledgeable in the art of polycondensation any number of polyethylene oxide polymers can be prepared containing a large variety of co-reactants, having preferably at least 10% by weight of polyethoxy-units which can be classified as hydrogels. Polycondensation hydrogels are described, for instance, in U.S. Pat. No. 3,822,238.

Also useful in this context are hydrogels prepared by free-radical initiated copolymerization of unsaturated polyesters based on maleic anhydride and alkylene diols with water-soluble vinyl monomers, vinyl pyrrolidone, 2-hydroxyethyl methacrylate, or hydroxy alkyl-vinylethers.

The hydrogels may also contain polysiloxane units, as described in U.S. Pat. No. 4,136,250, or contain perfluoro alkyl substituted side chains. Other useful substrates include water swellable polymers derived from natural products, such as cellulose or proteins, for example reconstituted cellulose films, and hydroxy-ethyl cellulose, or gelatin and albumin derived polymers.

In general, the term 'hydrogel' encompasses not only crosslinked water-swellable polymers, but also linear polymers which, like polyvinyl alcohol, dissolve only with difficulty or not at all in cold water, forming in effect a linear hydrogel. Even water soluble polymers can be used in the context of this invention as long as they do not dissolve during the reaction.

The most preferred hydrogel substrates for the purposes of carrying out this invention are hydrogel beads as they are obtained by suspension polymerization of hydroxyalkylacrylates or methacrylates, or N-vinylpyrrolidone containing mixtures. Such beads and the process for making them are described in copending U.S. application Ser. No. 911636 filed June 1, 1978, incorporated herein by reference.

In the context of this invention, a hydrogel is defined as a polymer having an effective degree of swelling in water of at least 5%.

The reactant pairs from which the GIPN phase is prepared are conveniently divided into reactant A, which is to be imbibed into the polymer substrate, and coreactant B, which is the diffusing reactant contained in the outside solution.

Most reactants can serve either as the internal reactant A portion of the pair, or as the external coreactant B portion. However, reactant A should possess a sufficiently low molecular weight in order to achieve practical loadings into the polymer substrate.

An alternative method, if the GIPN is synthesized by Diffusion Polycondensation in films, sheets, powder or hollow fibers is to bring reactant A in contact with one surface, while simultaneously reactant B is in contact with the other surface, resulting in a GIPN occupying more or less the center of the hydrogel sheet or film.

The following list gives a summary of the types of Diffusion-Polycondensates possible by combining reactant pairs with two or more of the following reactive groups:

| Functional Group of Reactant | | GIPN - type: Hydrogel Substrate with: |
|---|---|---|
| A (B) | B (A) | |
| —OH | —NCO | polyurethane |
| | —COOCO— | polyester |
| | —COCl | polyester |
| —NH$_2$, >NH | —NCO | polyurea |
| | —COOCO— | polyamide |
| | —COCl | polyamide |
| | $-\overset{O}{\underset{/\ \backslash}{C\!\!-\!\!\!-\!\!C}}-$ | epoxy-resin |
| —COOH | $-\overset{O}{\underset{/\ \backslash}{C\!\!-\!\!\!-\!\!C}}-$ | epoxy-resin |
| —NCO | $-\overset{O\ \ O}{\underset{}{\underset{\|\ \ \|}{COC}}}-$ | polyimides |

An especially useful, because practical, combination of reactants is diisocyanate and water, which is actually a version of the —NCO+NH₂ reaction since water first reacts with —NCO in the presence of a catalyst to form a primary amine.

Besides the classical polycondensation reactions listed above, other rapidly occurring chemical reactions can be used to carry out the process of this invention, for example:

(di-)aldehydes+amines to give poly-Schiff-bases; di-ketones or di-aldehyde+dihydrazine derivatives to give polyhydrazones; and base or free-radical catalyzed addition of dithiols to olefinic, acrylic or maleic compounds, like ethyleneglycoldiacrylate or poly-(propyleneglycol maleate).

Useful polyhydric alcohols, which can be used as reactant A or B include, but not by way of limitation, aliphatic and aromatic hydrocarbon diols of 1–10 carbon atoms such as ethylene glycol, propylene glycol, 1,3-butylene glycol, butane-1,4-diol, 2-butene-1,4-diol, 1,4-butyne diol, neopentyl glycol, 1,5-pentamethylene glycol, 1,6-hexamethylene glycol, decamethylene glycol, dimethylol-benzenes, dihydroxyethyl benzenes, 3-thia-1,5-pentane diol; glycerol, pentaerythritol, trimethylol propane; also sugars, like sorbitol, mannose, glucose, sucrose, lactose; diethylene glycol and polyalkylene oxide diols of structure where R₁ is methyl or hydrogen and n is 2–50; also tertiary amino groups containing diols like N-methyl diethanolamine or 3-pyridyl-1,5-pentane diol, bis-(2-hydroxyethyl) piperazine as well as alkylene oxide adducts of primary amines with 1–25 repeating alkoxy units and carboxy groups containing diols, like dihydroxy propionic acid.

The polyhydric alcohols may also be substituted by perfluoroalkyl groups as for instance disclosed in U.S. Pat. No. 3,935,277 and U.S. Pat. No. 4,001,305 and examplified by structures:

Halogen containing diols or polyols like: 2,3-dibromobutane diol; dibromoneopentyl glycol; 1-chloro-2,3-propane-diol; phosphorus and sulfur containing diols like 3-thiapentane-1,5-diol and Poly-primary and poly-secondary amines useful as reactants A or B include, but not by way of limitation 2–12 carbon atom aliphatic amines like ethylene diamine, 1,6-hexane-diamine, 2,4,4(2,2,4)trimethylhexane-1,6-diamine; piperazine; tetraethylene-pentamine, triethylene-tetramine and alkylene imine adducts to polyhydric alcohols like 2-aminopropyl ether terminated polyethylene and polypropylene oxides; also aminoalcohols like amino ethanol, 2-amino propanol, tris-(hydroxymethyl) amino methane; methyl-di(3-amino propyl) piperazine. Aromatic polyamines, like ortho, meta and para phenylene diamine, and bis-phenylenediamine, are also useful.

The diols and amines can be used alone or in combination with each other, the choice of a particular reactant depending on the second reactant to be used in preparing the IPN.

Diisocyanates useful as reactants A or B are, but not by way of limitation, aliphatic and aromatic diisocyanates, such as:

1,2-ethylene diisocyanate;
1,6-hexylene diisocyanate;
lysine diisocyanate;
bis(2-isocyanatoethyl) fumarate;
1,4-cyclohexylene diisocyanate;
methylcyclohexylene diisocyanate;
2,2,4(2,4,4)-trimethyl-1,6-hexylene diisocyanate;
2,6-toluene diisocyanate;
4,4′-diisocyanatodiphenyl ether;
4,4′-diisocyanatodiphenylmethane;
3,3′-dichloro-4,4′-diisocyanatodiphenylmethane;
4,4′-diphenyl diisocyanate;
4,4′-diisocyanatodibenzyl;
3,3′-dimethyl-4,4′-diisocyanatodiphenyl;
2,2′-dimethyl-4,4′-diisocyanatodiphenyl;
3,3′-dimethoxy-4,4′-diisocyanatodiphenyl;
2,2′-dichloro-5,5′dimethoxy-4,4′-diisocyanatodiphenyl;
3,3′-dichloro-4,4′-diisocyanatodiphenyl;
1,3-diisocyanatobenzene;
1,4-diisocyanatobenzene;
1,2-naphthylene diisocyanate;
4-chloro-1,2-naphthylene diisocyanate;
4-methyl-1,2-naphthylene diisocyanate;
1,3-naphthylene diisocyanate;
1,4-naphthylene diisocyanate;
1,5-naphthylene diisocyanate;
1,6-naphthylene diisocyanate;
1,7-naphthylene diisocyanate;
1,8-naphthylene diisocyanate;
4-chloro-1,8-naphthalene diisocyanate;
2,3-naphthylene diisocyanate;
2,7-naphthylene diisocyanate;
1,8-dinitro-2,7-naphthylene diisocyanate;
1-methyl-2,4-naphthylene diisocyanate;
1-methyl-5,7-naphthylene diisocyanate;
6-methyl-1,3-naphthylene diisocyanate;
7-methyl-1,3-naphthylene diisocyanate;
dimer acid diisocyanate (DDI, General Mills); and
isophorone diisocyanate.

Di-acid chlorides useful as reactants A or B include the chlorides of aliphatic di-carboxyacids of structure ClOC(CH$_2$)$_K$-COCl, where K is 0-18; unsaturated di-acid chlorides like fumaroyl chloride and aromatic di-acid chlorides: halogen substituted acid chlorides of aliphatic and aromatic di-carboxy acids. Typical examples are the di-acid chlorides of fumaric-, terephthalic-, succinic-, adipic-, sebacic-, glutaric acids.

Dialdehydes useful as reactants A or B include ortho- and para-dibenzaldehyde, glutaraldehyde, glyoxal.

Anhydrides useful as reactants A or B are, but not by way of limitation, maleic-, succinic-, alkenyl-succinic-, phthalic-, tetrahydrophthalic-, norbornene-, methyl norbornene-, trimellitic and chlorendic-anhydride; also dianhydrides, like benzophenone tetracarboxylic acid dianhydride, benzene-tetracarboxylic acid dianhydride, tetrahydrofuran tetracarboxylic acid dianhydride etc. Useful substituted anhydrides are for instance the addition products of alkyl thiols and alkyl thiols substituted by perfluoroalkyl groups, siloxane groups, carboxy groups to maleic or norbornene anhydrides, like Where R is methyl or hydrogen and R$_f$ is perfluoroalkyl of 3 to 18 carbon atoms Reactant A can be incorporated into the hydrogel matrix by simply immersing the polymer in it, if A is a swelling agent for the polymer. Otherwise a solvent, which will dissolve the reactant and swell the polymer has to be used. Similarly, during the reaction step, if reactant B has too little solvent power to diffuse into the polymer, a solvent or solvent mixture is necessary to aid diffusion or control the reaction. Solvents useful during the loading and reaction steps must be of course non-reactive, that is free of reactive hydrogens (—OH, NH$_2$) or groups which could react with such hydrogens (—COCl; —NCO). Useful solvents are ketones, like acetone, methyl-ethyl ketone, methyl-propyl ketone, methyl-butyl ketone, methyl-isobutyl ketone and homologs; ethers, like diethyl ether, ethylene glycol dimethyl ether; diethylene glycol-dimethyl ether, di-ethyl and dibutyl carbitol; esters like ethyl acetate, methyl cellosolve acetate; ethyl cellosolve acetate; cyclic ethers like tetrahydrofurane and dioxane; amides and cyclic amides, like dimethyl formamide and N-methyl-pyrrolidone; sulfolane; chlorinated hydrocarbons, like chloroform, carbon tetrachloride, FREONS, tetrachloroethylene, dichloromethane, trichloroethylene, 1,1,1-trichloroethane etc; chlorobenzene or di-chlorobenzenes; aliphatic hydrocarbon like hexane, heptane, octane, up to octadecane, and aromatic hydrocarbons like benzene, toluene, xylene.

It is permissible to use double bonds containing solvents of all the above mentioned classes, since double bonds do not normally interfere with poly-condensation reactions, for example: vinyl ketones; vinyl ethers, alkylacrylates and alkyl methacrylates (or the corresponding amides); N-vinyl pyrrolidone; styrene or vinyl esters like vinyl-acetate.

The choice of solvents during the reaction depends on ones objective: if it is desired that the diffusion rate be fast, a good swelling agent for the polymer should be chosen; if it is desired that the diffusion rate be slowed down, a poor swelling agent is important. Often it is advantageous to use varying combinations of a good and a poor swelling agent, methyl ethyl ketone and heptane for instance, to achieve a controllable range of reaction conditions.

If the reactant is by itself a swelling agent, or solvent than no solvent is necessary at all during the reaction.

If too much solvent is present the polycondensation reaction is slowed down by the dilution effect and whatever modification occurs extends deep into the polymer.

To a large extent the depth of penetration and the sharpness of the gradient is also influenced by the miscibility of both reactants; good miscibility leads to deep and diffuse modified region, poor miscibility to dense and sharp, narrow membranes.

Also, the reactant A should be chosen such that it is not reactive with the hydrogel substrate under the reaction conditions. Also, the coreactant B should be chosen such that it is much more reactive with reactant A than the hydrogen substrate. However, a minor amount of crosslinking through grafting is not necessarily undesirable.

Also, the choice of the reactant A, and the coreactant B, is guided by the selection of a condensation polymer which is less permeable than the hydrogel substrate itself. As a result, the interpenetrating less permeable condensation polymer forms the rate controlling membrane therein.

The process of treating hydrogel beads or particles consists basically of two steps: first, loading the hydrogel with reactant A; second, reaction with coreactant B. Other operations, such as drying off the solvent after loading or washing out excess reactants after the second step are also usually carried out but can be omitted in special cases. Loading the hydrogel polymer with reactant A can be done with or without solvent, depending on chemical nature and molecular size of the reactant. Degree of swelling with reactant A, defined as $$DS_A = \frac{\text{weight of swollen gel} - \text{w.o dry gel}}{\text{weight of dry gel}}$$

can vary from 5 to 500% preferably between 20 and 300% and most preferred between 25 and 200%. If a solvent is used and not driven off after loading, then DS$_{solvent}$ (DS$_s$)+DS$_A$ can vary from 50 to 1000%. Sometimes it is advisable not to dry off the solvent, but form the membrane on a highly swollen polymer, because it is then easier for it to withstand the stress of subsequent contractions or expansions. It does not matter in this case if the swelling is due only to reactant A or to a combination of A with one or more solvents; carrying out the reaction in a highly swollen state to enhance resistance of the membrane to stress is thus another embodiment of the invention. Simultaneously with loading reactant A, other compounds can be incorporated into the polymer, such as: catalysts which would promote the polycondensation reaction; active ingredients, like a herbicide molluscicide, bacteriostat, pesticide; fertilizer; dyestuffs; fragrances, etc.

After the polymer containing the reactant A has been removed from the loading solution it is rinsed free of surface material and dried, if this is deemed necessary. Following this the polymer is immersed in coreactant B, or a solution of coreactant B in one or more solvents. Such solvents have been described above and they are for this step selected according to their ability to swell the polymer. Good solvents will increase the extent of the reaction and penetration of B into the polymer, poor solvents will hamper it. The structure and function of the membranized surface is thus dependent on the reaction medium. The ratio of polymer to reaction medium will depend on the physical form of the polymer to be treated; if round hydrogel beads are the substrate the reaction is preferably carried out in a stirred reaction vessel under dry conditions if necessary ($N_2$; $CO_2$) with a polymer to liquid ratio of 1:3 to 1:20. Exact temperature control is very important to get reproducibility, as are exact levels of catalysts. Reaction temperatures can vary from room temperature to 150° C., reaction times from a few minutes to 20 hours. The extent of the reaction, as measured by weight gain, is not linear with time, but levels off after a certain reaction time, because the forming IPN membrane starts acting as a diffusion barrier for reactants A and B.

After the reaction is finished, the polymer is taken out of the solution, its surface is rinsed and then it is washed free of excess reactants by a good solvent, preferably in a continuous flow extractor or a Soxhlet-type apparatus. Any of the solvents mentioned as useful for the previous two steps can be used, but it has been found that even reactive solvents, such as methanol or ethanol can be used to leach out, for instance, diisocyanate-glycol reactant pair; in this case it is important that either the diisocyanate-methanol reaction is very slow compared to the washing rate or that the reaction product is itself soluble in the washing solvent. Coreactant B is usually washed out earlier, since it exists more in the surface layer, while reactant A is removed last. It is therefore entirely practical to divide the washing operation into two steps, using the most practical solvent for each reactant. It is one of the great advantages of this invention, that the product can be washed under as many different conditions and for as long a time as is found necessary to remove any impurities which might interfere with its safety in a bio-medical application.

On the other hand, situations exists where reactant A need not to be washed out at all, either because it is a harmless compound, for instance a sugar, in the intended application, or it is by itself an active ingredient, for instance a herbicide in a herbicidal application.

After the washing operation the polymer is dried to constant weight and can be stored until used.

The process of treating sheets, films or hollow fibers can in principle be the same as the one described to treat round beads, but in addition can consist in simply contacting both sides simultaneously with reactant A and B respectively under conditions which allow diffusion and reaction to occur. The reaction occurs more or less in the center of the substrate, sometimes in a very narrow region, and if the substrate can be later dissolved the polycondensate can be isolated as a self-supporting thin film or membrane.

In form of films, membranes, or hollow fibers, the products of this invention are especially useful in membrane-separation processes, such as reverse osmosis, dialysis, electrophoresis, solvent-water separations processes as they are used during waste water treatment and facilitated-transport.

In addition, hydrogels treated according to the process of this invention show a reduced rate of water loss in dry air and have surfaces which are hardened and strengthened by the presence of the IPN.

Active ingredients are imbibed into the modified hydrogels by immersing the polymer in solutions of the active agents in solvents or solvent mixtures which are good swelling agents for the polymer for instance ethanol, ethanol-water mixtures, or methylene chloride. Of course, if the active agent is a liquid and by itself a swelling agent for the polymer, no solvent is necessary. After maximum loading of actives has been achieved, the solvent is recovered in vacuo.

Any of the drugs used to treat the body, both topical and systemic, can be incorporated as the active agent in the copolymeric carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug, the desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided, for example, anabolics, e.g. methandrostenolone; analgesics, e.g. acetylsalicylic acid, phenylbutazone or methadone; androgens, e.g. methyltestosterone; antibiotics, e.g. rifampin; antidepressants, e.g. imipramine or maprotiline; antidiabetics; e.g. phenformin; anticonvulsives, e.g. carbamazepine; anti-histamines, e.g. tripelennamine; antihypertensives, e.g. hydralazine; antiinfectives, e.g. trimethoprim; antiparasitics, e.g. nifurtimox; antiparkinson agents, e.g. levodopa; anti-phlogistics, e.g. naproxen; antitussives, e.g. benzonatate; appetite depressants, e.g. mazindol; bronchodilators, e.g. fenoterol; coronary dilators, e.g. fenalcomine; corticoids, e.g. dexamethasone; cytostatics, e.g. floxuridine; diuretics, e.g. hydrochlorothiazide; hypnotics, e.g. glutethimide; neuroleptics, e.g. reserpine or thioridazine psychoanaleptics, e.g. methylphenidate; tranquilizers, e.g. diazepam; uricosurics, e.g. sulfinpyrazone; vasodilators, e.g. isoproterenol.

In addition to drugs, there can be incorporated in the copolymers of the instant invention fragrances or food flavors, such asorange oil, citral, coffee, tea, lemon oil, synthetic lemon-lime flavor, strawberry flavor, vanilla, biacetyl, anise, lilac fragrance, pine fragrance, peppermint oil, oily orchids essence, anethole, ethylpropionate, ethyl acetate, acetaldehyde, menthol and spearmint, as well as pesticides including bactericides, fungicides, insecticides and nematocides, as well as herbicides.

Other examples for said biologically effective ingredients are listed in U.S. Pat. No. 3,660,563 (columns 3 to 7).

The membrane modified hydrogel devices of this invention are best characterized by swelling and diffusion measurements. The following describes the terms and measurements with hydrogel beads as substrates, which are used in the examples to characterize and at the same time establish the usefulness of the modified polymers.

$DL_A$ = degree of loading in reactant $A$ (%)

$$= \frac{\text{weight of polymer swollen in } A - \text{dry weight}}{\text{dry weight}}$$

$WG$ = weight gain of polymer during reaction (%)

$$= \frac{\text{dry weight after reaction} - \text{dry weight before reaction}}{\text{dry weight before reaction}}$$

$t_S 50$ (90) = time to reach 50% (90%) of final $DS$ in ethanol (hours)

$DS$ = Degree of swelling (%)

$$= \frac{\text{volume of swollen polymer} - \text{dry volume}}{\text{dry volume}}$$

$DA$ = degree of loading with active ingredient (%)

$$= \frac{\text{weight of loaded polymer} - \text{empty polymer weight}}{\text{empty polymer weight}}$$

$t_D 50$ (90) = time for polymer to release 50% (90%) of its active ingredients.

$DL_A$, $WG$, $DA$ are determined gravimetrically, $t_s$ and $DS$ are determined by measuring the volume change of hydrogel beads during swelling in ethanol with a burette. $DA$ and $t_D$ are determined by continuously monitoring the increase in UV absorption due to the active ingredient released from the loaded beads into a reservoir (water) circulating through a flow-through UV-cell.

The following examples are intended as only illustrative, and are not intended to limit the nature or scope of the invention. All parts are by weight unless otherwise indicated.

EXAMPLE 1

Synthesis of Hydrogel Beads:

A mixture consisting of 35 parts 2-hydroxyethyl methacrylate (HEMA), 45 parts N-vinylpyrrolidone (NVP) and 20 parts poly-n-butyleneoxidediol of MW 2000, capped with 2 moles isophorone-diisocyanate (IPDI) and fully reacted with HEMA (=macromer) was polymerized as a suspension in an aqueous salt solution using Mg(OH)$_2$ as a suspending agent, as described in detail in copending application Ser. No. 911636. The resulting round beads were rinsed, washed, dried and the $-16 +18$ mesh fraction was screened out. This polymer has a $DS_{H2O}$ of 105%, $DS_{Ethanol} = 200\%$.

Loading with Reactant A:

50 g of hydrogel beads with the above composition and size ($-16 +18$ mesh) were equilibrated in a 50% solution of trimethylolpropane (TMP) (=A) in methyl ethyl ketone at 50° C. for 20 hours. Then they were filtered, rinsed with MEK and dried in vacuo (10 mm Hg) for 7 hours at 50° C. Their $DL_A$ (degree of loading was 132%. The loaded beads were tacky, but became hard and dry to the touch after being cooled to 0° C. for several hours.

Formation of IPN-Membrane:

5 g of the TMP-loaded hydrogel beads were suspended in a solution of 25 g 2,2,4(2,4,4)-trimethylhexane-1,6-diisocyanate (TMDI) (B) in 25 g MEK and containing 12 mg triethylamine (TEA) and 6 mg dibutyltindilaurate (DBTL) as catalysts, and stirred in a flask equipped with reflux-condenser and nitrogen sparge for 3 hours at 50° C. A nitrogen sparge was mainted throughout the reaction.

The beads were filtered off, rinsed with MEK and extracted in a Soxhlet extractor with MeOH for 24 hours. The extraction of reactants A and B was followed by gas chromatography, which showed that all unreacted TMDI is washed out very fast, followed by the extraction of unreacted TMP. After the extraction is completed the beads were dried in vacuo (1 mm Hg) at 50° for 8 hours. Their weight gain during the reaction was determined gravimetrically to be 49%.

Optical microscopy showed that all of the IPN was concentrated in a narrow (~0.05 mm) ring within the polymer surface.

EXAMPLES 2 and 3

5 g of the TMP loaded hydrogel beads prepared in Example 1 were treated as in Example 1 with TMDI (50% in MEK) for various times; the results of Examples 1-3 are given below:

| Ex. No. | Reaction Time (hours) | IPN Weight Gain (%) |
|---|---|---|
| 1 | 3 | 49 |
| 2 | 5 | 71 |
| 3 | 7 | 82 |

These data show how the membrane formation as measured by the IPN-weight gain is dependent on reaction time.

EXAMPLES 4–8

5 g of beads prepared and loaded as in Example 1 were treated as in Example 1, but for 5 hours and with various concentrations of TMDI in MEK. The results are shown below:

| Ex. No. | % MEK | IPN Weight Gain (%) |
|---|---|---|
| 8 | 0 | 9 |
| 4 | 20 | 14 |
| 2 | 50 | 71 |
| 5 | 60 | 21 |
| 6 | 66 | 13 |
| 7 | 80 | 7 |

These data show the importance of the solvent to effect diffusion of the reactant TMDI. By choosing various TMDI/MEK ratios one can influence extent and structure of the IPN membrane.

EXAMPLES 9-11

5 g of beads, prepared and loaded with TMP as described in Example 1, were treated with an 80% solution of TMDI in MEK at 50° C. for 5 hours. A catalyst mixture of triethylamine and DBTL (2:1 by weight) was used in varying amounts.

| Ex. No. | $DL_A$ | Catalyst (%) | IPN Weight Gain (%) |
|---|---|---|---|
| 9 | 129 | 0.015 | 80 |
| 10 | 126 | 0.058 | 39 |
| 11 | 126 | 0.035 | 14 |

These data show that an increase in catalyst concentration increases the reaction rate.

EXAMPLES 12-14

5 g of beads prepared and loaded as described in Example 1 were treated with a 50% solution of TMDI in MEK for 5 hours at various temperatures. 0.035% catalyst mixture (triethylamine/DBTL=2/1 by weight) was used.

| Ex. No. | Temp. (°C.) | Weight Gain (%) |
|---|---|---|
| 12 | 30 | 5 |
| 13 | 40 | 24 |
| 14 | 50 | 71 |

These examples show how increasing reaction temperature increases thereaction rate.

EXAMPLES 15 and 16

5 g each of hydrogel beads as prepared in Example 1 were loaded with trimethylolpropane from a MEK solution to 136 and 183% $DL_A$. After drying they were reacted with a 50% solution of TMDI in MEK at 50° C. for 5 hours. Their weight gain was determined.

| Example | $DL_A$ | IPN Weight Gain (%) |
|---|---|---|
| 15 | 136 | 15 |
| 16 | 183 | 42 |

As expected, the IPN weight gain is higher with a higher concentration of reactants.

2.5 g of beads as prepared in Examples 1-16 were put into absolute ethanol and their rate of swelling was followed volumetrically in a modified dilatometer. $t_s-50$, $t_s-90$ and DS were determined. Another 1 g sample each of beads from Examples 1-16 was loaded with a drug and the release rate measured.

Figure 1:
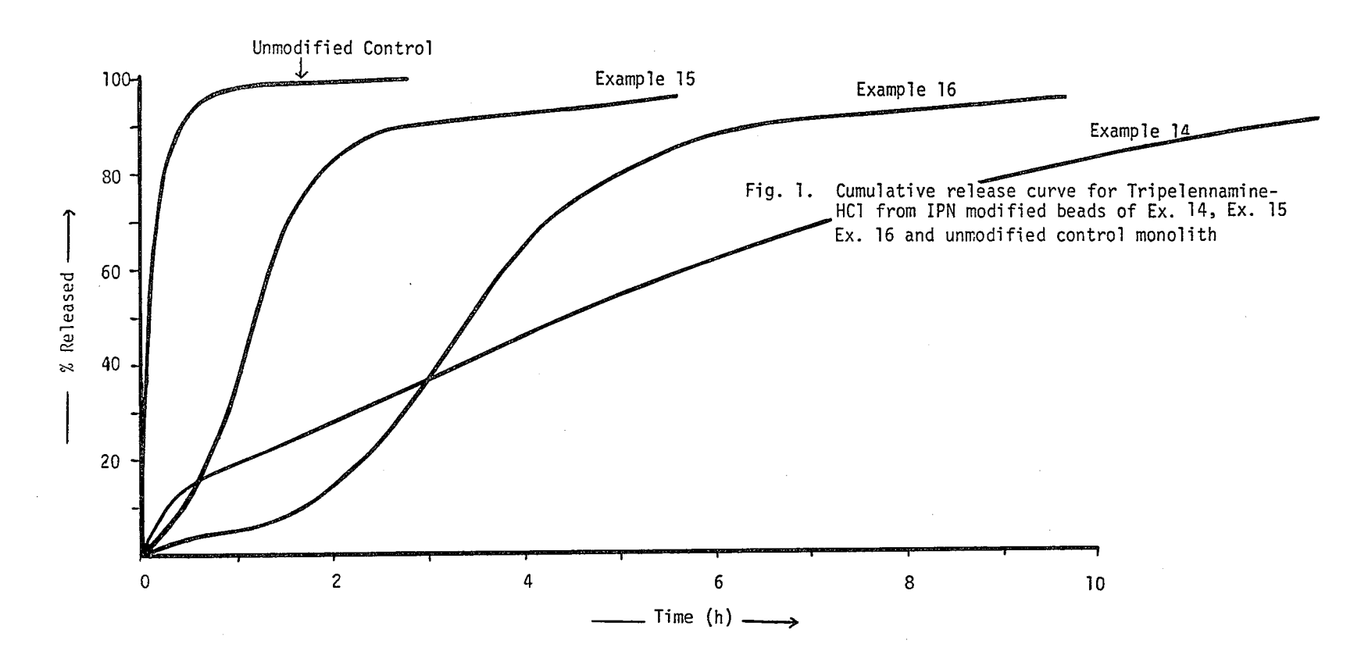
FIGS. 1 and 2 illustrate the exceptional retardation in drug release and the long periods of near zero-order release rates obtained by the membranes of the present invention.
Figure 2:
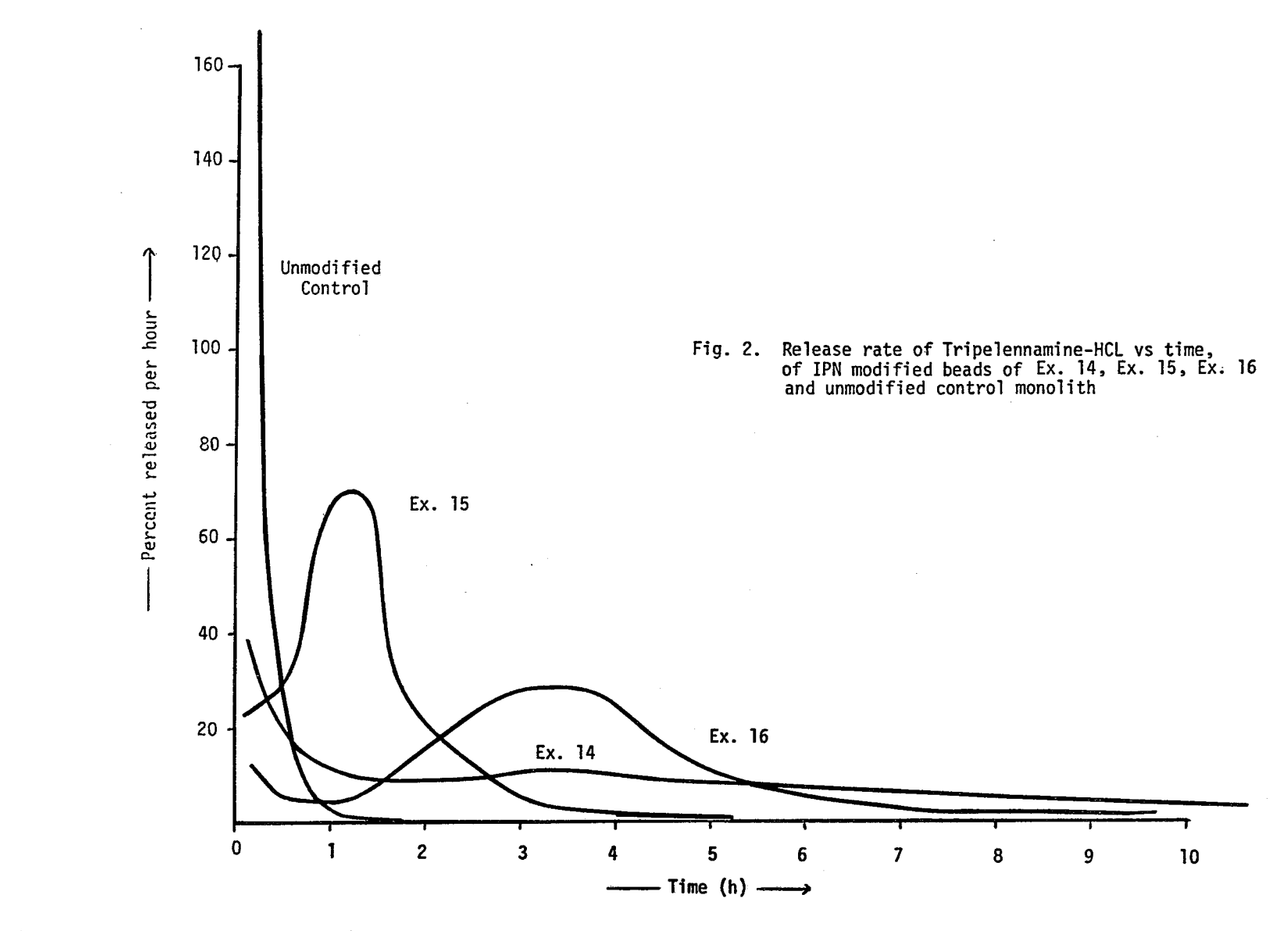

The drug release curves of Examples 14-16 and of unmodified controls were plotted on graph paper (FIGS. 1-2). Those figures illustrate the exceptional retardation in drug release and the long periods of near zero-order release rates obtained.

Example 17

| Ex. No. | Variable | IPN Weight Gain (%) | Ethanol Swelling | | | Drug[1] Diffusion | | |
|---|---|---|---|---|---|---|---|---|
| | | | $t_s50$ hours | $t_s90$ | DS % | DA % | $t_D50$ hours | $t_D90$ |
| 1 | Time | 49 | 4.5 | 9.8 | 162 | 37 | 9.2 | 23 |
| 2 | | 71 | >5.5 | — | 138 | 26 | 14.0 | — |
| 3 | | 82 | >5.5 | — | 120 | 22 | 15.2 | — |
| 4 | MEK | 14 | 0.3 | 2.3 | 173 | 117 | 0.25 | 2.90 |
| 5 | | 21 | 4.2 | 5.9 | 176 | 84 | 1.30 | 12.00 |
| 6 | | 13 | 1.4 | 2.3 | 156 | 55 | 1.19 | 2.05 |
| 7 | | 7 | 2.5 | 6.0 | 203 | 25 | 1.15 | 1.55 |
| 8 | | 9 | 0.9 | 3.0 | 195 | — | — | — |
| 9 | Catalyst | 80 | — | — | 164 | — | — | — |
| 10 | | 39 | 1.60 | 4.1 | 181 | 61 | 2.35 | 5.22 |
| 11 | | 14 | 0.30 | 2.3 | 173 | 117 | 0.25 | 2.90 |
| 12 | Temp. | 5 | 0.70 | 1.90 | 174 | 75 | 0.25 | 0.75 |
| 13 | | 24 | 1.47 | 2.57 | 151 | 60 | 1.45 | 3.25 |
| 14 | | 71 | >5.5 | | 144 | 24 | 4.59 | 12.20 |
| 15 | $DS_A$ | 15 | 1.65 | 3.10 | 185 | 25 | 1.10 | 2.30 |
| 16 | | 49 | 5.4 | 6 | 170 | 25 | 3.00 | 6.00 |
| Control | — | 0 | 0.33 | 1.33 | 205 | 25 | 0.12 | 0.37 |

[1] In Examples 1-3 Phenformin—HCl was used, in all other examples Tripelennamine—HCl was used.

EXAMPLES 18-22

5 g of each of hydrogel beads prepared by suspension polymerization as described in Example 1 (−14 +16 mesh) and loaded with trimethylolpropane to a $DL_A$ of 60%, were exposed to various reactants B under the conditions listed below. IPN weight-gain was measured as well as DS in ethanol.

2 g of each sample was subsequently loaded with drug (Tripelennamine-HCl) and the diffusion rate was measured.

| Ex. | Reactant B | Reaction Conditions | | IPN Weight Gain % | DS (%) Ethanol | DA % | (min) | |
|---|---|---|---|---|---|---|---|---|
| | | Time (min) | Temp (°C.) | | | | $t_D50$ | $t_D90$ |
| 18 | Toluene diisocyanate 50% in heptane | 265 | 60 | 9 | 103 | 59 | 40 | 146 |
| 19 | Maleic anhydride 50% in MEK | 60 | 90 | 12 | 100 | 57 | 17 | 60 |
| 20 | Isophorone diisocyanate 50% in MEK; N(C₂H₅)₃ as catalyst | 250 | 50 | 35 | 172 | 53 | 79 | 663 |
| 21 | 4,4'-diisocyanato-diphenylmethane: 40% | 30 | 50 | 11 | 160 | 62 | 34 | 170 |

|     |           | Reaction Conditions | | IPN Weight Gain | DS (%) | | | (min) | |
|-----|-----------|------|------|------|---------|------|---------|---------|---------|
| Ex. | Reactant B | Time (min) | Temp (°C.) | % | Ethanol | DA % | $t_{D50}$ | $t_{D90}$ | |

| Ex. | Reactant B | Time (min) | Temp (°C.) | % | Ethanol | DA % | $t_{D50}$ | $t_{D90}$ |
|-----|-----------|------|------|----|-----|----|-----|-----|
|     | heptane: 14% MEK: 46% | | | | | | | |
| 22  | Same | 60 | 50 | 18 | 195 | 57 | 157 | 253 |
| Control | None | | | | 195 | 68 | 7 | 43 |

EXAMPLES 23–35

Synthesis of Hydrogel Beads: By suspension—polymerization in aqueous salt solution and using MG(OH)$_2$ as suspending agent, polymer beads with various compositions were synthesized; the resulting round beads were rinsed, washed, dried and the −16 +18 mesh fraction was screened out.

Loading with Reactant A: 5 g each of thus obtained polymer beads and including beads of Ex. 1 were equilibrated in solutions of trimethylolpropane (TMP), hexanediol (HD) and butanediol (BD) in MEK and their degree of loading with these reactants (DL$_A$) determined as described in Ex. 1. The following table lists the polymers with their degree of swelling in water and their degree of loading with various reactants A:

| Ex. No. | Composition | | | DS (%) | | Reactant A | DL$_A$ (%) |
|---------|------|---------|-----|------|------|-----------|-----|
|         | Hema | Macromer | NVP | H$_2$O | Eth. | | |
| 23 | 10 | 15 | 75 | 211 | 283 | TMP | 190 |
| 24 | " | " | " | " | " | HD | 184 |
| 25 | 20 | 30 | 50 | 95 | 204 | TMP | 184 |
| 26 | " | " | " | " | " | HD | 127 |
| 27 | " | " | " | " | " | BD | 163 |
| 28 | 35 | 20 | 45 | 105 | 200 | TMP | 152 |
| 29 | " | " | " | " | " | HD | 118 |
| 30 | " | " | " | " | " | HD | 118 |
| 31 | 45 | 20 | 35 | 107 | 129 | HD | 115 |
| 32 | " | " | " | " | " | BD | 99 |
| 33 | 80 | 20 | — | 52 | 107 | TMP | 97 |
| 34 | " | " | " | " | " | HD | 53 |
| 35 | " | " | " | " | " | BD | 105 |

FORMATION OF IPN MEMBRANES 5 g of each of the reactant A—loaded beads obtained in this manner were suspended and stirred under nitrogen in a solution of 10 g 2,2,4-trimethyl-1,6-hexanediisocyanate (TMDI) in 10 g MEK and containing dibutyltindilaurate as catalyst of 50° C. for 5 hours. After that time the beads were filtered off, rinsed with MEK and extracted in a Soxhlet extractor with MEK for 24 hours, as described in Ex. 1. After extraction the beads were dried in vacuo (1 mm Hg) at 50° C. for 8 hours and their weight-gain determined.

With the dried beads ethanol-swelling measurements were carried out and a 1 g sample from each experiment was loaded with a drug by imbibing the beads with a 50% solution of the drug in water-ethanol (40/60) mixture, followed by drying in vacuo (1 mm Hg) at room temperature.

The following table shows the results of the reaction and drug-release measurements. (T=TRASICOR: P=Tripelennamine-HCl)

TABLE
Drug Release from Various Gradient-Polyurethane-IPN Modified Hydrogel Beads

| Ex. No. | Polymer | Reactant A | DBTL % | IPN % | Drug Release | | |
|---------|---------|-----------|--------|-------|------|------|------|
|         |         |           |        |       | DA % | $t_{50}$ | $t_{90}$ |
| 23 | 1015 | TMP | 0.015 | 60 | T 47 | 2.43 | 8.44 |
| 24 | 1015 | HD | 0.05 | 20 | T 99 | — | — |
| 25 | 2030 | TMP | 0.015 | 32 | T 52 | 0.90 | 2.62 |
| 26 | 2030 | HD | 0.05 | 30 | T 55 | 0.31 | 1.08 |
| 26 | 2030 | HD | 0.05 | 30 | T 55 | 0.68 | 2.03 |
| Control | 2030 | — | — | — | T 85 | 0.09 | 0.48 |
| 28 | 3520 | TMP | 0.015 | 51 | P 21 | 10.2 | 27.8 |
| 29 | 3520 | HD | 0.05 | 29 | P 31 | 0.74 | 2.35 |
| 30 | 3520 | BD | 0.10 | 40 | P 21 | 3.32 | 6.75 |
| Control | 3520 | — | — | — | P 78 | 0.25 | 0.60 |
| 31 | 4520 | HD | 0.1 | 38 | T 21 | 7.30 | 25.0 |
| 32 | 4520 | BD | 0.1 | 43 | | | |
| Control | 4520 | — | — | — | T 79 | 0.33 | 0.90 |
| 33 | 8020 | TMP | 0.015 | 12 | T 25 | 3.14 | 7.06 |
| 34 | 8020 | HD | 0.05 | 19 | T 25 | 4.26 | 9.27 |
| 35 | 8020 | BD | 0.05 | 18 | T 27 | 4.80 | 9.92 |
| Control | 8020 | — | — | — | T 19 | 0.38 | 1.39 |

EXAMPLES 36–38

5 g samples of polymer beads prepared according to Example were were loaded with halogenated diols:

| | | |
|---|---|---|
| dibromoneopentyl glycol | (DBNG) | DL$_A$ = 143% |
| 2,3-dibromobutenediol | (DBBG) | DL$_A$ = 121% |
| 3-chloro-1,2-propanediol | (CPD) | DL$_A$ = 199% |

The loaded samples were reacted as described in a 50% solution of TMDI in MEK; after washing and drying they were loaded with a drug and then release rate determined. The results are tabulated below.

TABLE
Drug Release from Gradient-Polyurethane Modified Hydrogel Beads

| Ex. No. | Reactant A | DBTL % | IPN % | DA % | Drug Release[1] (h) | |
|---------|-----------|--------|-------|------|------|------|
|         |           |        |       |      | $t_{D50}$ | $t_{D90}$ |
| 36 | DBNG | 0.10 | 33 | 25 | 2.2 | 6.3 |
|    |      | 0.05 | 20 | 42 | 0.6 | 2.0 |
| 37 | DBBG | 0.10 | 39 | 17 | 2.7 | 9.0 |
|    |      | 0.05 | 31 | 31 | 0.4 | 1.2 |
| 38 | CPD  | 0.1  | 23 | 62 | 0.4 | 1.1 |
| Control | | | | 68 | 0.1 | 0.75 |

[1]Tripelennamine-HCl

EXAMPLES 39–43

According to the suspension polymerization process described in Example 1 polymer beads of the following composition were synthesized: HEMA: 21%; NVP: 27%; n-butylacrylate: 40%; macromer as described in Example 1: 12%; their DS$_{H_2O}$ was 15%; DS$_{Ethanol}$=216%.

1.0 g of these beads (18 mesh fraction) were imbibed with TMDI to a $DL_A$ of 100%. The TMDI loaded beads were filtered, rinsed with MEK and stirred for 1 hour at 50° C. in 10 g water containing 0.005 g triethylamine as catalyst and 0.1% TRITON X-100 to insure good wetting of the polymer. Some evolution of gas ($CO_2$) was observed. The beads were filtered, stirred with MEK and extracted in a Soxhlet with MEK for 24 hours. Aftery drying in vacuo their IPN weight gain was found to be 75%, all in form of a narrow ring in the polymer surface (by microscopy under polarized light).

Using the modifications described below, other polyurea IPN's were prepared and gave the IPN weight gains listed in the table:

| Ex. No. | Deviation from Ex. 39 | IPN-Weight Gain |
|---|---|---|
| 40 | 0.5% DABCO | 39 |
| 41 | 0.5 h at 50° C. | 33 |
| 42 | 4 h at 50° C. | 108 |
| 43 | 0.5% DABCO at 25° C. | 22 |

EXAMPLE 44

1 g of 18-mesh beads synthesized according to Example 39 were imbibed with TMDI to a $DL_A$ of 100%. After filtration and rinsing they were stirred for 1 hour at 50° C. in a 10% solution of 2,4,4(2,2,4)trimethylhexane-1,6-diamine in water. The beads were then filtered off, rinsed and Soxhlet-extracted with MEK for 24 hours. Their IPN-weight gain was 28%, distributed in a narrow ring within the polymer surface.

EXAMPLES 45 AND 46

Two 5 g samples of polymer beads with the composition described in Example 39 were swollen in water (Ex. 45) and a 0.5% aqueous solution of triethylamine (Ex. 46). After filtration the swollen beads were once rinsed with MEK, followed by stirring in 100% TMDI at 50° C. for 2 hours. They were then filtered, rinsed with MEK and extracted in Soxhlet with MEK for 18 hours. After drying their IPN-weight gain was found to be zero % (Ex. 45) and 23% (Ex. 46) respectively. The IPN layer of Ex. 46 extended ~ 0.05 mm into the polymer, as determined by optical microscopy.

EXAMPLE 47

10 g of +18-20 mesh polymeric beads with the composition: 21% HEMA; 26% NVP, 40% N-butylacrylate, 12% macromer as described in Example 1 and containing 1% dimethylamino ethyl methacrylate were swollen in water to equilibrium ($DS_{H_2O}=27$), filtered and stirred in 100% TMDI at 50° C. for 1½ hours. After filtration and drying an IPN-weight gain of 32% was obtained, distributed in a narrow ring in the bead surface.

This example is similar to Example 45 and 46, except that no external catalyst was used. As is shown, the bound tert. amino groups act instead as an immobilized catalyst for the polymer formation.

EXAMPLE 48

2 g of the polymer beads from Ex. 39 and containing 2% water were stirred in ISONATE-143L (a carbodiimide containing dimer of 4,4'-diisocyanato diphenylmethane, from Upjohn Chem. Co.) at 50° C. for 1 hour. Then the beads were filtered, rinsed with MEK and Soxhlet extracted with MEK for 18 hours. After drying the IPN-weight gain was found to be 13%, distributed in an approx. 0.05 mm thick surface layer.

EXAMPLE 49

The process of Ex. 48 was repeated, but instead of 100% ISONATE a 50% solution of ISONATE in MEK was used. 33% IPN weight-gain was obtained, distributed almost uniformly throughout the polymer.

EXAMPLE 50

1 g of 18-mesh beads synthesized according to Example 39 were imbibed with a 5% solution of sebacoyl chloride in dichloromethane solvent to a $DL_A$ of 435%. After filtration and solvent re-equilibration they were stirred for 0.7 hr at 25° C. in a 10% solution of 2,2,4-(2,4,4)-trimethylhexane-1,6-diamine in water. The beads were then soxhlet-extracted with acetone for 24 hours. Their IPN-weight gain was 21%, distributed in a narrow ring within the polymer surface.

EXAMPLES 51-54

A one mm thick polymer sheet was prepared by polymerizing a mixture 50% 2-hydroxyethylmethacrylate (Hema) and 50% of a macromer derived from a polysiloxane-polyethyleneoxide block copolymer diol of MW. 2000[1] by successive capping with (1) IPDI, (2) Hema, in bulk between Mylar lined glass plates. A 1×5 cm strip of this polysiloxane hydrogel sheet was swollen in butanediol to a $DL_A$ of 49%, rinsed with MEK and immersed in a 50% solution of TMDI in MEK at 50° C. for 0.5, 1.5 and 3.0 hours. 0.015% DBTL was used as catalyst. (Ex. 51-53)

Another 1×5 cm strip was loaded with TMP to a $DL_A$ of 45% and reacted for $3^h$ at 55° C. in a 50% TMDI in MEK solution with 0.045% DBTL. (Ex. 54)

After rinsing extracting and drying cross sections of the polymer were swollen in water and viewed under the microscope under polarized light. Well defined IPN-membranes could be seen which were absent from the original polymer and had the following thicknesses

| Ex. | Reaction Time (h) | Radius-Depth of | |
|---|---|---|---|
| | | IPN-Region (mm) | Core Region |
| 51 | 0.5 | 0.025 | 0.47 |
| 52 | 1.5 | 0.030 | 0.46 |
| 53 | 3.0 | 0.080 | 0.39 |
| 54 | 3.0 | 0.200 | 0.30 |

[1]DOW CORNING Silocone, reactive fluid Q-3667

EXAMPLE 55

1.2 g of +18 mesh polymer beads synthesized according to Example 25 were swollen in thiodiglycol to a $DL_A$ of 191%. After filtration and rinsing they were stirred in a solution of 12 g 2,2,4-(2,4,4)-trimethyl-1,6-hexanediisocyanate (TMDI), in 12 g methyl ethyl ketone (MEK) and containing 0.05% dibutyltindilaurate as catalyst for 5 hours at 50° C. The beads were then filtered off, rinsed with MEK, and soxlet-extracted with MEK for 24 hours. After drying their IPN-weight gain was 41% distributed in a narrow ring within the polymer surface.

EXAMPLE 56

2 g of hydrogel beads as prepared in Example 1 were loaded with a 50% solution of HYSTL G-1000 (an hydroxy terminated polybutadiene) in 1-methyl-2-pyrrolidone (M-Pyrol) to a $DL_A$ of 33%. They were then reacted with a 50% solution of 2,2,4-(2,4,4)-trimethylhexane-1,6-diisocyanate (TMDI) in M-Pyrol and containing 0.03% dibutyltindilaurate as catalyst for 5 hours at 50° C. The beads were then filtered off, rinsed with methylethyl ketone (MEK) and soxhlet-extracted for 24 hours with MEK, then 24 hours with methanol. After drying their IPN-weight gain was 35% distributed in a narrow ring in the polymer surface.

EXAMPLE 57

A 0.11 mm thick polyvinyl alcohol film was heat sealed into a 10 cm long and 1.5 cm wide pouch. The pouch was filled with a 10% solution of terephthalaldehyde in a mixture of DMF, MEK, methanol and water and immersed in a 10% solution of paraphenylenediamine in the same solvent mixture. During standing at room temperature for 16 hours the polymer turned slowly yellow-orange. The pouch was emptied, opened up and the polymer was rinsed in MEK-methanol and soaked in water for 4 hours. Cross sections of the dry film under the microscope revealed that about ½ of the thickness of the original PVA film was occupied by the yellow-orange reaction product, the poly-[Schiff-base]:

in form of an IPN with polyvinyl-alcohol, while the other half of the film had remained colorless.

(A PVA film immersed in a terephtaldehyde or phenylenediamine solution alone, did not change color or appearance, nor did IR spectroscopy indicate any reaction between PVA and reactants).

A part of the GIPN-modified PVA film was slowly stirred in 80° C. water until all PVA had dissolved, leaving behind a yellow-brown, thin, self-supporting polymeric membrane of 0.01 mm thickness and considerable strength.

EXAMPLE 58

The process of Example 57 was repeated, using a clamped-off tube of reconstituted cellulose film of 0.04 mm thickness. After 16 hours reaction-time the film was rinsed with MEK and soaked in water for 5 hours. The film had turned deep yellow-orange and, when viewed through the microscope, revealed a 0.004 mm thick colored layer of reaction product in the center of the film. This indicates that the polycondensation occurred in a narrow region of the cellulose matrix, where mixing of both reactants took place.

EXAMPLES 59 AND 60

1 g of 18-mesh beads synthesized according to Example 39 were imbibed with a 50% solution of triisocyanate T-1890 (from Veba-Chemie) in dry acetone for 10 minutes (Ex. 59) and 15 minutes (Ex. 60). The beads were filtered and then reacted immediately in a 10 g aqueous solution containing 0.1 g triethylamine as catalyst and 0.1% Triton X-100 to insure good wetting of the polymer for 1 hour at 50° C. The beads were then filtered off, rinsed and soxhlet extracted with MEK for 20 hours. After drying their IPN weight gain was found to be 3.9% (Ex. 59) and 10.1% (Ex. 60) distributed in narrow ring within the polymer surface.

We claim:

1. A non-uniform substantially water-insoluble interpenetrating polymer blend composition comprising a water swellable first polymer substrate interpenetrated in a gradient substantially normal to the substrate surface by a less permeable condensation second polymer to form a diffusion rate controlling membrane therein.

2. A composition according to claim 1, wherein said water swellable first polymer is cellulose, or a homopolymer or copolymer containing units of vinyl alcohol, acrylamide, hydroxyalkyl-acrylate or—methacrylate, vinylpyrrolidone, or hydroxyalkyl-vinyl ether,—maleate or—fumarate or a polyethyleneoxide diol containing polycondensate, with the proviso that sufficient said units are incorporated, such that said first polymer is swellable to an extent of at least 5% by weight in water.

3. A composition according to claim 1, wherein said less permeable condensation second polymer is an aliphatic or aromatic polyurethane, polyester, polyamide, polyimide, polyurea or polyimine.

4. A composition according to claim 2, wherein said less permeable condensation second polymer is an aliphatic polyurethane or aliphatic polyurea.

5. A composition according to claim 2, wherein said water swellable first polymer is cellulose, polyvinyl alcohol, or a copolymer of hydroxyethyl-methacrylate and N-vinylpyrrolidone crosslinked with isophoronediisocyanate capped polytetramethylene oxide and with or without a $C_1$-$C_{18}$ alkyl-acrylate or —methacrylate comonomer.

6. A composition according to claim 5, wherein said less permeable condensation second polymer is an aliphatic polyurethane or aliphatic polyurea.

7. A composition according to claim 1, which is in the form of a bead having an average diameter between about 0.05 mm and 4 mm.

8. A composition according to claim 7, wherein said water swellable first polymer is cellulose, or a homopolymer or copolymer containing units of vinyl alcohol, acrylamide hydroxyalkyl-acrylate or—methacrylate, vinylpyrrolidone, or hydroxyalkyl-vinyl ether,—maleate or—fumarate or a polyethyleneoxide diol containing polycondensate, with the proviso that sufficient said units are incorporated such that said first polymer is swellable to an extent of at least 5% by weight in water.

9. A composition according to claim 7, wherein said water swellable first polymer is cellulose, polyvinyl alcohol, or a copolymer of hydroxyethyl-methacrylate, and N-vinylpyrrolidone crosslinked with isophoronediisocyanate capped polytetramethylene oxide and with or without a $C_1$-$C_{18}$ alkyl-acrylate or—methacrylate comonomer.

10. A composition according to claim 1, which is in the form of a sheet, tube or pouch.

11. A composition according to claim 10, wherein the sheet, tube or pouch has a well thickness between about 0.01 mm and 5 mm.

12. A composition according to claim 11, wherein the composition is a tube in the form of a hollow fiber.

13. A composition according to claim 7, wherein there is contained within said bead an active ingredient selected from the group consisting of a drug, herbicide, insecticide or fragrance.

14. A water actuated diffusion type active agent dispenser including a means for dispensing a dosage of active agent into an aqueous fluid environment, comprising a bead of a substantially water insoluble water swellable first polymer interpenetrated by a diffusion rate controlling membrane parallel to the surface of said bead, said membrane consisting essentially of said first polymer interpenetrated by a less permeable condensation second polymer, said membrane forming an inclosure for said active agent to continuously dispense said agent at a controlled and continuous rate by diffusion across the membrane.

15. A dispenser according to claim 14, wherein at least part of said active agent is a drug.

16. A dispenser according to claim 14, wherein said first polymer is cellulose, or a homopolymer or copolymer containing units of vinyl alcohol, acrylamide hydroxyalkylacrylate or—methacrylate, vinylpyrrolidone, or hydroxyalkylvinyl ether,—maleate or—fumarate or a polyethyleneoxide diol containing polycondensate, with the proviso that sufficient said units are incorporated such that said first polymer is swellable to an extent of at least 5% by weight in water.

17. A dispenser according to claim 16, wherein said second polymer is an aliphatic or aromatic polyurethane, polyester, polyamide, polyimide, polymer or polyimine.

18. A dispenser according to claim 17, wherein at least part of said active agent is a drug.

19. A composition according to claim 11, in the form of a sheet.

20. A composition according to claim 11, wherein said first polymer is cellulose or polyvinyl alcohol.

* * * * *